US007252686B2

(12) United States Patent
Carrison et al.

(10) Patent No.: US 7,252,686 B2
(45) Date of Patent: Aug. 7, 2007

(54) METHODS FOR REDUCING BONE COMPRESSION FRACTURES USING WEDGES

(75) Inventors: Harold F. Carrison, Pleasanton, CA (US); Stanley W. Olson, Jr., San Ramon, CA (US); Lex P. Jansen, Pleasanton, CA (US)

(73) Assignee: Boston Scientific Scimed, Maple Grove, MN (US)

( * ) Notice: Subject to any disclaimer, the term of this patent is extended or adjusted under 35 U.S.C. 154(b) by 624 days.

(21) Appl. No.: 10/639,871

(22) Filed: Aug. 13, 2003

(65) Prior Publication Data

US 2005/0038517 A1 Feb. 17, 2005

(51) Int. Cl.
*A61F 2/44* (2006.01)
(52) U.S. Cl. .................................................. 623/17.16
(58) Field of Classification Search ........ 623/17.11–16
See application file for complete search history.

(56) References Cited

U.S. PATENT DOCUMENTS

| | | | |
|---|---|---|---|
| 4,349,921 A | 9/1982 | Kuntz | |
| 4,404,327 A | 9/1983 | Crugnola et al. | |
| 4,650,489 A | 3/1987 | Thompson | |
| 4,881,536 A | 11/1989 | Noble et al. | |
| 5,514,137 A | 5/1996 | Coutts | |
| 5,529,736 A | 6/1996 | Shalaby et al. | |
| 5,586,985 A | 12/1996 | Putnam et al. | |
| 5,645,084 A | 7/1997 | McKay | |
| 5,718,707 A | 2/1998 | Mikhail | |
| 5,925,051 A | 7/1999 | Mikhail | |
| 6,030,390 A | 2/2000 | Mehdizaddeh | |
| 6,124,373 A | 9/2000 | Peter et al. | |
| 6,206,924 B1 * | 3/2001 | Timm ...................... | 623/17.16 |
| 6,241,734 B1 | 6/2001 | Scribner et al. | |
| 6,387,130 B1 * | 5/2002 | Stone et al. ............. | 623/17.16 |
| 6,395,007 B1 | 5/2002 | Bhatnagar et al. | |

(Continued)

FOREIGN PATENT DOCUMENTS

WO   WO 03/059180   7/2003

OTHER PUBLICATIONS

PCT International Search Report for PCT/US2004/012975, Applicant: Scimed Life Systems, Inc., Forms PCT/ISA/210 and 220, dated Sep. 8, 2004 (7 pages).

(Continued)

*Primary Examiner*—Eduardo C. Robert
*Assistant Examiner*—Annette Reimers
(74) *Attorney, Agent, or Firm*—Vista IP Law Group, LLP

(57) ABSTRACT

Devices, kits, and methods are provided for treating a bone structure, e.g., a vertebra, with a compression fracture. Wedges can be introduced into the bone structure in a direction that is lateral to the compression fracture, and stacked on tope of each to apply forces to the bone structure to reduce the compression fracture. The wedges can be introduced into the bone structure using a cannula. The wedges can be introduced as wedge pairs, in which case, a subsequent wedge pair can be introduced between a previously introduced wedge pair in order to drive the previously introduced wedges apart to create the stacking arrangement. Optionally, the wedges can be provided with longitudinal bores, in which case, they can be introduced into the bone structure, over a guide member that is threaded through the bores.

35 Claims, 14 Drawing Sheets

U.S. PATENT DOCUMENTS

| | | | |
|---|---|---|---|
| 6,488,710 B2 * | 12/2002 | Besselink | 623/17.15 |
| 6,540,784 B2 | 4/2003 | Barlow et al. | |
| 6,595,998 B2 | 7/2003 | Johnson et al. | |
| 7,037,339 B2 * | 5/2006 | Houfburg | 623/17.11 |
| 2002/0183761 A1 | 12/2002 | Johnson et al. | |
| 2003/0078661 A1 * | 4/2003 | Houfburg | 623/17.11 |
| 2003/0139812 A1 | 7/2003 | Garcia et al. | |
| 2003/0171812 A1 * | 9/2003 | Grunberg et al. | 623/17.11 |
| 2004/0010314 A1 | 1/2004 | Matsuzaki et al. | |
| 2004/0267366 A1 * | 12/2004 | Kruger | 623/17.16 |
| 2005/0055097 A1 * | 3/2005 | Grunberg et al. | 623/17.11 |
| 2005/0107878 A1 * | 5/2005 | Conchy | 623/17.11 |
| 2005/0159815 A1 * | 7/2005 | Kamimura et al. | 623/17.11 |

OTHER PUBLICATIONS

PCT Written Opinion of the International Search Authority for PCT/US2004/012975, Applicant: Scimed Life Systems, Inc., Form PCT/ISA/237, dated Sep. 8, 2004 (7 pages).

* cited by examiner

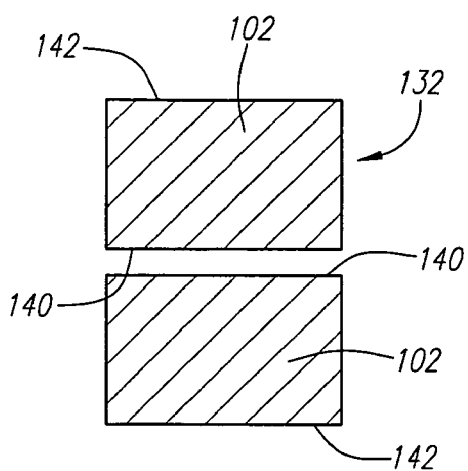
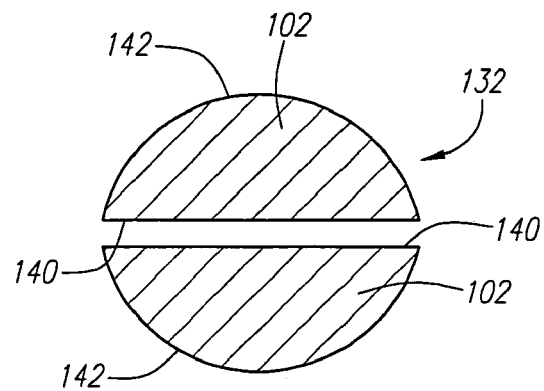
FIG. 6          FIG. 7
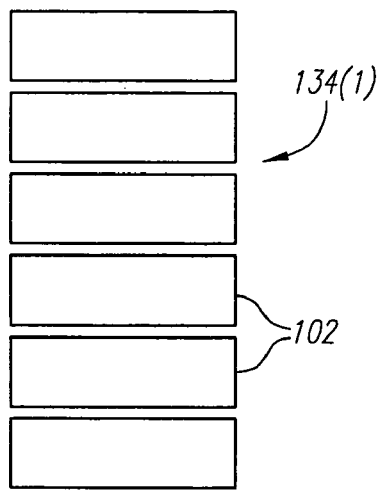
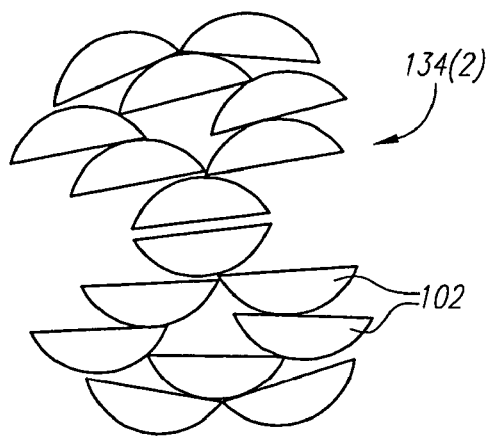
FIG. 8          FIG. 9
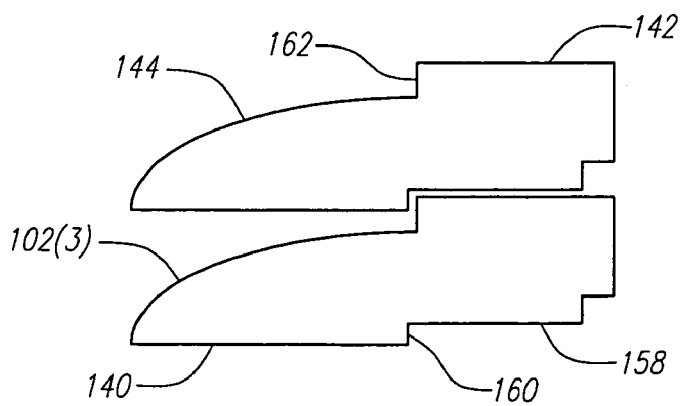
FIG. 10

METHODS FOR REDUCING BONE COMPRESSION FRACTURES USING WEDGES

FIELD OF THE INVENTION

The invention relates to the treatment of bone structures, such as vertebrae, and in particular, to the reduction and stabilization of bone compression fractures.

BACKGROUND OF THE INVENTION

Spinal injuries, bone diseases, such as osteoporosis, vertebral hemangiomas, multiple myeloma, necrotic lesions (Kummel's Disease, Avascular Necrosis), and metastatic disease, or other conditions can cause painful collapse of vertebral bodies. Osteoporosis is a systemic, progressive and chronic disease that is usually characterized by low bone mineral density, deterioration of bony architecture, and reduced overall bone strength. Vertebral compression fractures (VCF) are common in patients who suffer from these medical conditions, often resulting in pain, compromises to activities of daily living, and even prolonged disability.

FIG. 1 illustrates three vertebrae 10, 12, and 14, each with an anterior side 16, a posterior side 18, and lateral sides 20 (only one shown). Vertebrae 10 and 14 are fully intact, while vertebra 12 has a VCF 22 (i.e., the top 24 and bottom 26 of the vertebra 12 have been displaced towards each other). The force required to reduce the VCF 22 (i.e., to displace the top 24 and bottom 26 of the vertebra 12 back to their original positions) can often be rather high. Present needles for use within vertebrae bend or deform in the presence of lateral force, and thus, are not rigid enough to reduce VCF's. Balloons can be placed in the fractured vertebra and expanded to reduce the VCF. Such balloons can expand equally in all radial directions, however, which can cause the vertebra to shatter on the anterior, posterior, and lateral sides.

Consequently, there is a significant need to provide an improved means for reducing bone compression fractures, e.g., VCF's.

SUMMARY OF THE INVENTION

In accordance with a first aspect of the present inventions, a wedge-shaped device for reducing a bone fracture (e.g., compression fractures in metaphyseal bony tissues, such as vertebrae, tibial (shin bone) plateau, femoral (thigh bone) metaphyses, calcaneal (heel), and humeral (shoulder) indications) is provided. The wedge-shaped device comprises a rigid body that is composed of a biocompatible material, such as, e.g., polymethylmethacrylate (PMMA), and is sized to fit within the fractured bone structure, e.g., a vertebra. Multiple wedge-shaped devices can be stacked to provide a force that reduces a compression fracture within the bone structure.

To this end, the rigid body has a leading side, a lagging side opposite the leading side, and a tapered side between the leading and lagging sides. In the preferred embodiment, the tapered and leading sides form a point so that, e.g., the wedge-shaped device can be easily inserted between two other wedge-shaped devices. In the preferred embodiment, the leading and lagging sides are also substantially parallel to each other to, e.g., facilitate stacking of wedge-shaped devices on top of each other. The rigid body may also comprise a driven side between the leading and lagging sides opposite the tapered side. A notch can be formed between the leading and driven sides, so that, e.g., a pair of the wedge-shaped devices, when placed back-to-back (i.e., with their leading edges engaging each other) can be more easily be split apart by another wedge pair, thereby facilitating stacking of the wedges. The rigid body may also comprise another notch formed along the leading side that complements the lagging side. In this case, distal movement of a wedge-shaped device relative to another wedge-shaped device can be limited when the lagging edge of one wedge is slid within the notch of the leading edge of another wedge.

In accordance with a second aspect of the present inventions, a kit for reducing a bone fracture (e.g., a vertebral bone fracture) is provided. The kit comprises a plurality of wedges, each of which may be similar to the wedge-shaped device described above. The kit further comprises a cannula having a lumen sized to fit a pair of the wedges when the leading sides of the wedge pair engage each other. The kit lastly comprises a wedge driver configured for pushing the wedge pair through the cannula lumen. In one embodiment, each wedge has a notch formed between the leading and driven sides, so that the notches of a wedge pair form an indentation. In this case, the wedge driver may comprise a protuberance shaped to engage the indentation.

The kit may also comprise another plurality of wedges, each having substantially parallel opposing sides, a blunted side between the opposing sides, and a driven side between the opposing sides and opposite the blunted side. The blunted side of these wedges reduces the risk of injuring the distal side of the bone structure. The kit may include an optional plunger assembly configured to be introduced within the cannula lumen. As an example, the plunger assembly can be used to convey treatment media, e.g., bone cement, through the cannula lumen into the bone structure.

In accordance with a third aspect of the present inventions, a method of treating a bone structure having a compression fracture (e.g., a vertebral compression fracture) is provided. The method comprises introducing pairs of wedges into the bone structure in a direction lateral to the compression fracture, wherein a subsequently introduced wedge pair is placed between a previously introduced wedge pair, such that that preceding pairs of wedges are displaced in opposite directions towards the respective opposing sides of the bone structure. In the preferred method, the opposing sides of the bone structure are displaced in opposite directions as each subsequently introduced wedge pair is placed between an intermediate previously introduced wedge pair. The wedge pairs may be introduced into the bone structure until the compression fracture has been completely reduced.

The wedges may be introduced into the bone structure by inserting a cannula into the bone structure, and then introducing the wedge pairs through the cannula into the bone structure. The wedge pairs may be introduced through the cannula by pushing the wedge pairs with a wedge driver. The method may optionally include introducing treatment media into the bone structure after introduction of the wedge pairs.

In accordance with a fourth aspect of the present inventions, a wedge-shaped device for reducing a bone fracture (e.g., a vertebral compression fracture) is provided. The wedge-shaped device comprises a biocompatible body having a leading side, a lagging side opposite the leading side, and a tapered side between the leading and lagging sides. The wedge-shaped device additionally comprises a longitudinal bore that extends through the biocompatible body, e.g., from the driven side to the tapered side of the body. Although the present invention should not be so limited in its broadest aspects, the longitudinal bore allows the wedge-shaped device to be introduced over a guide member into a bone cavity. The cross-sectional shape of the bore can be any suitable shape, but in the preferred embodiment, is non-circular (e.g., oval). In this manner, the wedge-shaped device can be more easily rotationally aligned with respect to the guide member.

In accordance with a fifth aspect of the present inventions, a kit for reducing a bone fracture (e.g., a vertebral compression fracture) is provided. The kit comprises a plurality of biocompatible wedges, each of which has a bore extending therethrough, and a guide member sized to fit through the bore. Although the present invention should not be so limited in its broadest aspects, the use of a guide member, as opposed to a cannula, minimizes the size of the access passage through which the guide member can be introduced into the bone structure, thereby minimizing the trauma caused to the bone structure. Alternatively, the size of the wedges can be maximized without increasing the size of the access passage.

The kit may optionally comprises a wedge driver configured for pushing each wedge over the guide member. Preferably, the wedge driver comprise a bore, in which case, the guide member is sized to fit through the bore of the wedge driver. Although the present invention should not be so limited in its broadest aspects, the guide member is preferably laterally rigid to provide a more controlled delivery of the wedges. The cross-sectional shapes of the bore and guide member can be any suitable shape, but in the preferred embodiment, are non-circular (e.g., oval) for the reasons previously described.

In accordance with a sixth aspect of the present inventions, a method of treating a bone structure having a compression fracture (e.g., a vertebral compression fracture) is provided. The method comprises introducing a guide member into the bone structure, and introducing wedges over the guide member in a direction lateral to the compression fracture, e.g., by pushing the wedges with a wedge driver that is itself introduced over the guide member. The wedges are introduced into the bone structure, such that a subsequently introduced wedge is placed in contact with a previously introduced wedge. As a result, previously introduced wedges are displaced in a direction towards one or both of the opposing sides of the bone structure. Because a guide member is used to introduce the wedges into the bone structure, any access passage made in the bone structure can be minimized, or alternatively, the size of the wedges can be maximized. The method may optionally include introducing treatment media into the bone structure after introduction of the wedges.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIG. 6 is a cross-sectional view of a wedge that can be used in the treatment kit of FIG. 2;

FIG. 7 is a cross-sectional view of another wedge that can be used in the treatment kit of FIG. 2;

FIG. 8 is a lateral view showing a linear wedge stacking arrangement that can be constructed using a plurality of wedges similar to the wedge of FIG. 6;

FIG. 9 is a lateral view showing a distributed wedge stacking arrangement that can be constructed using a plurality of wedges similar to the wedge of FIG. 7;

FIG. 10 is a lateral view of optional embodiments of wedges that can be used in the kit of FIG. 2;

DETAILED DESCRIPTION OF THE PREFERRED EMBODIMENTS

Figure 1:
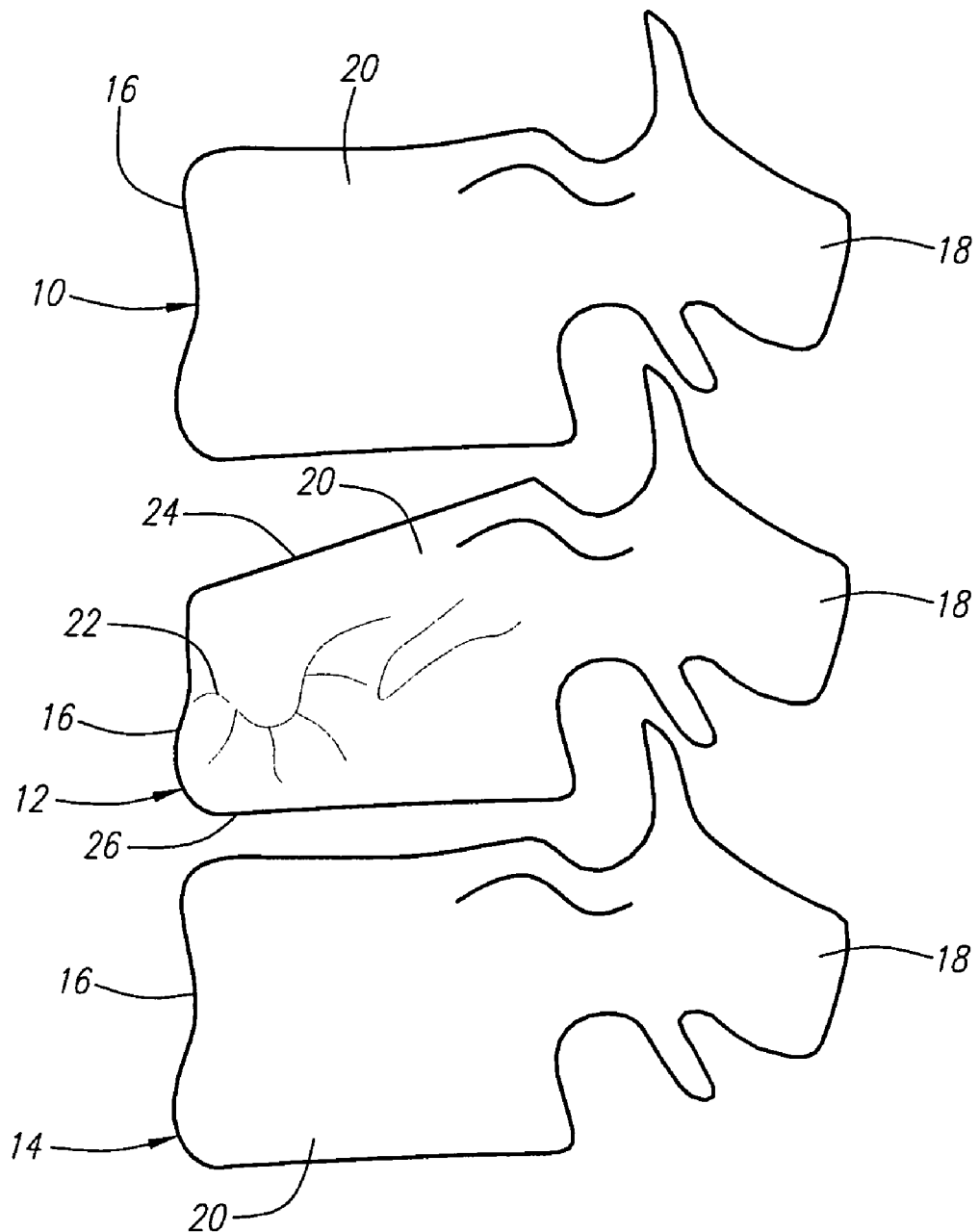
FIG. 1 is a lateral view of three vertebra, two of which are normal, and one of which has a compression fracture.
Figure 2:
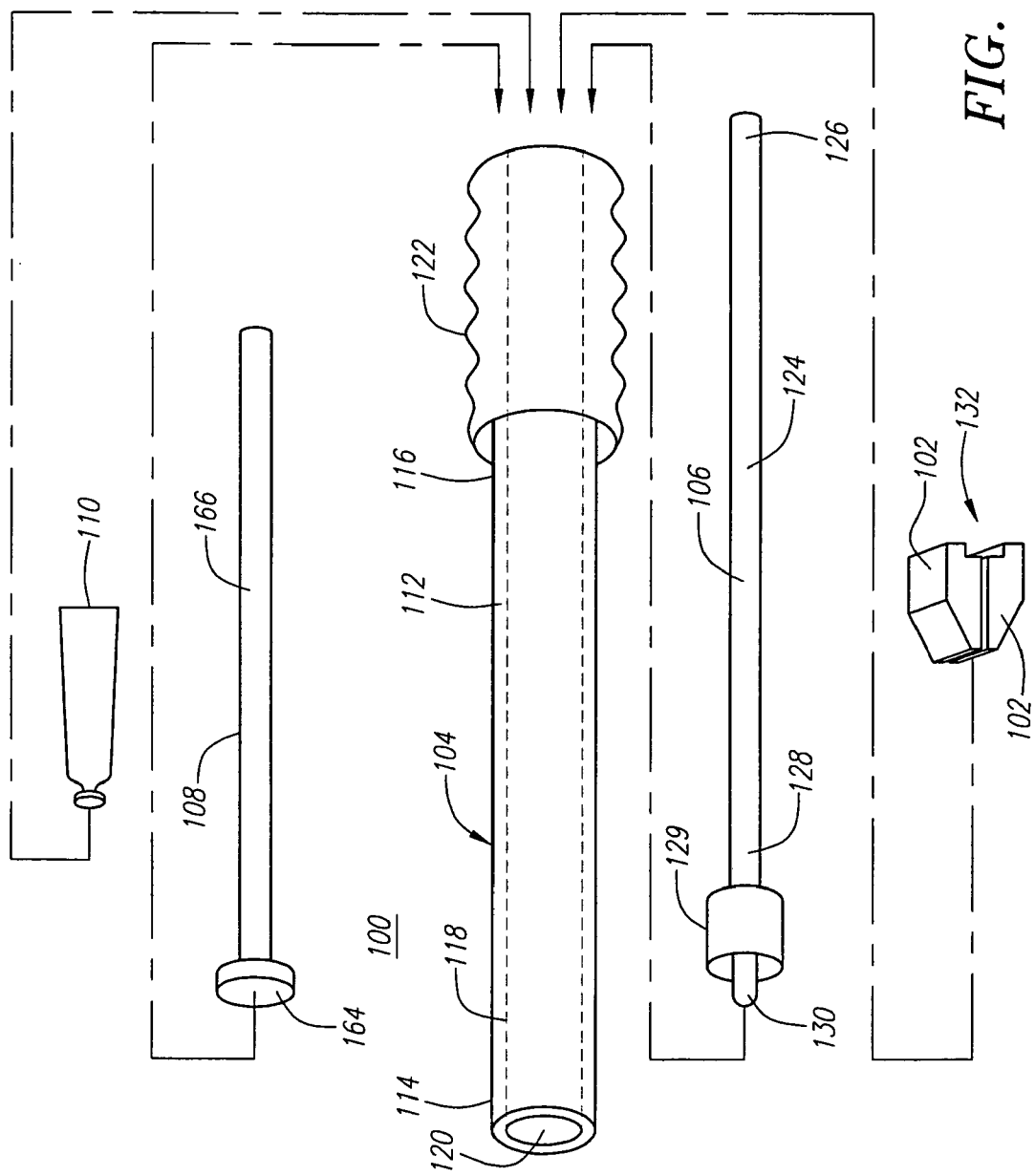
FIG. 2 is a plan view of a bone fracture treatment kit constructed in accordance with a preferred embodiment of the present inventions.

Referring to FIG. 2, a bone fracture treatment kit 100 constructed in accordance with one preferred embodiment of the present inventions is illustrated. The kit 100 can be used for treating a bone compression fracture, and specifically, a compression fracture 202 within a vertebra 200 (shown in FIGS. 13-18). The kit 100 generally comprises a plurality of fracture reducing wedges 102 (shown in FIG. 2 as a pair of wedges 102), a delivery member, and specifically a cannula 104, for delivery of therapeutic agents (e.g., the wedges 102 and a therapeutic medium) into the vertebra 200, a wedge driver 106 for pushing the wedges 102 through the cannula 104 into the vertebra 200 in order to reduce the compression fracture 202, and an optional plunger assembly 108 for forcing a therapeutic medium 110 through the cannula 104 and into the vertebra 200 in order to stabilize and set the vertebra 200.

Referring still to FIG. 2, the cannula 104 comprises a shaft 112 having a distal end 114 and proximal end 116, a lumen 118 terminating in an exit port 120 at the distal end 114 of the cannula shaft 112, and a handle 122 mounted on the proximal end 116 of the cannula shaft 112. To facilitate introduction into the bone structure vertebra 200, the cannula shaft 112 is preferably stiff (e.g., it can be composed of a stiff material, or reinforced with a coating or a coil to control the amount of flexing), so that the cannula shaft 112 can penetrate the vertebra 200 without being damaged. The materials used in constructing the cannula shaft 112 may comprise any of a wide variety of biocompatible materials. In a preferred embodiment, a radiopaque material, such as metal (e.g., stainless steel, titanium alloys, or cobalt alloys) or a polymer (e.g., ultra high molecular weight polyethylene) may be used, as is well known in the art. Alternatively, if supported by a rigid member during introduction into the vertebra 200, the cannula shaft 112 may be flexible.

The outer diameter of the cannula shaft 112 is preferably less than ½ inch, although other dimensions for the outer diameter of the cannula shaft 112 may also be appropriate, depending on the particular application or clinical procedure. The cannula lumen 118 should have an inner diameter so as to allow wedge pairs 132 (as illustrated in FIG. 2) to be delivered within the lumen 118, as will be described in further detail below. In the illustrated embodiment, the cross-sectional profile of the cannula lumen 118 is circular, but can be other shapes as well.

For example, the cross-sectional profile can be a generally smaller oval shape that minimizes patient trauma, while preserving the space necessary to deliver the wedges 102. This may be particularly useful if the cross-sectional profile of the wedge pair 132 is oval-shaped, such as the wedge pair 132 illustrated in FIG. 7. For example, the largest dimension of the oval-shaped cross-section can be used to pass the largest cross-sectional dimension of the wedge pair 132 (typically, the dimension extending along the interface between the wedges 102), while the smaller dimension of the oval-shaped cross-section can be used to pass the smaller cross-sectional dimension of the wedge pair 132 (typically, the dimension extending perpendicular to the interface between the wedges 102). When inserting the cannula shaft 112 within a bone structure, the longer cross-sectional dimension can be inline with the direction of the bone growth. That is, the direction of bone growth in a vertebra is in the direction of the spine. As such, the longer cross-sectional dimension should be inline with the direction in which the spine extends when the cannula shaft 112 is inserted into the vertebra 200. In this manner, a cannula shaft 112 with a larger total cross-sectional area can be used without sacrificing additional bone strength in the direction of bone cell growth. In addition to reducing trauma, a cannula lumen 118 with an oval-shaped cross-section facilitates alignment of the wedge pairs 132 therein due to the non-constant circumferential shape of the lumen 118. Triangular and rectangular cross-sectional profiles can also be used for this purpose.

In the illustrated embodiment, the distal tip of the cannula shaft 112 is blunt. In this case, the thickness and cross-sectional profile of the cannula shaft 112 is small enough, so that the distal tip can be used as a cutting or deforming tool for boring or coring through bone structure. Alternatively, the distal tip of the cannula shaft 112 may be advantageously sharpened or wedged to facilitate its introduction into the bone structure. Even more alternatively, a stilette (not shown) can be introduced through the cannula lumen 118 to provide an independent means for boring through the bone structure. In this manner, bone cores will not block the cannula lumen 118, which may otherwise prevent, or at least make difficult, subsequent delivery of the wedges 102 and other therapeutic materials.

The wedge driver 106 comprises a driver shaft 124 having a proximal end 126 and distal end 128, a driver head 129 formed at the distal end 128 of the shaft 124, and a protuberance, specifically a ridge 130, formed on the distal face of the driver head 129. The ridge 130 facilitates engagement of the wedge driver 106 with wedge pairs 132, as will be described in further detail below. The wedge driver 106 is sized to slide within the cannula lumen 118 and may be composed of any suitable rigid material, e.g., any of a wide variety of materials, such as plastics, nitinol, titanium, and alloys. In a preferred embodiment, a radiopaque material such as metal (e.g., stainless steel, titanium alloys, or cobalt-chrome alloys) is used. Alternatively, a polymer, such as an ultra high molecular weight polyethylene, may also be used to construct the wedge driver 106.

Figure 3:
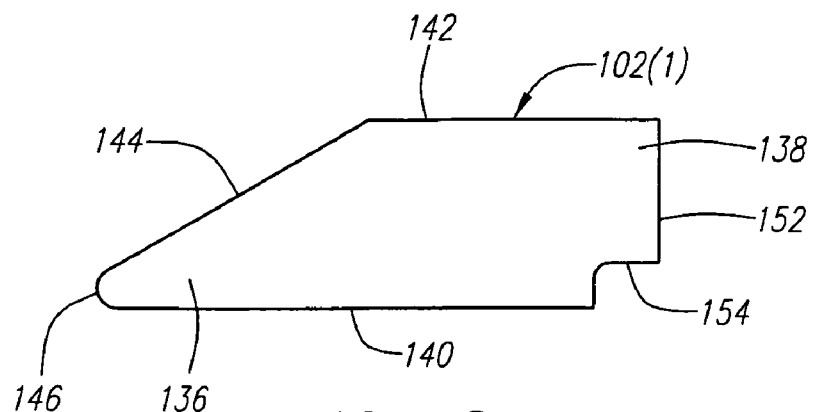
FIG. 3 is a tapered wedge that can be used in the treatment kit of FIG. 2.
Figure 4:
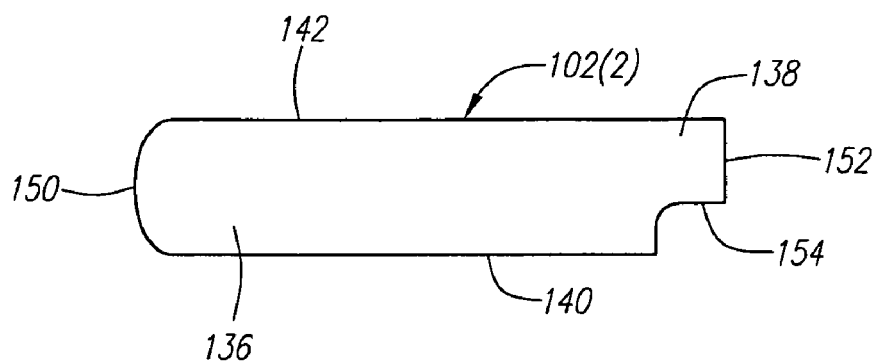
FIG. 4 is a blunt-nosed wedge that can be used in the treatment kit of FIG. 2.
Figure 5:
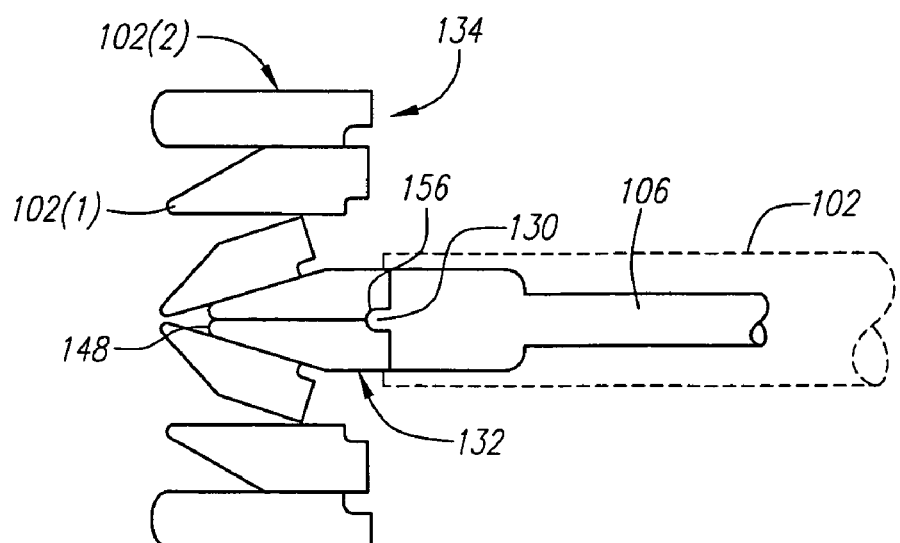
FIG. 5 is a lateral view showing one implementation of stacking the wedges of FIGS. 3 and 4.

Referring now to FIGS. 3-5, the fracture reducing wedges 102 are configured to implanted into the vertebra 200, and are thus, preferably composed of a rigid biocompatible material, such as, e.g., polymethylmethacrylate (PMMA). The wedges 102 are shaped, such that when introduced into the vertebra 200 as wedge pairs 132, the wedges 102 can be slid between each other to form a wedge stack 134, the height of which increases with each addition of a wedge pair 132. Each wedge 102 comprises a proximal end 136 and a distal end 138, i.e., the distal end 138 of the wedge 102 is designed to be introduced into the vertebra 200 first, and the proximal end 136 of the wedge 102 is designed to be introduced into the vertebra 200 last.

As illustrated in FIGS. 3 and 4, there are two types of wedges 102: a tapered wedge 102(1) and a blunt-nosed wedge 102(2). Each of the wedges 102 comprises an opposing pair of first and second sides 140 and 142. In the case of the tapered wedge 102(1), the first side 140 extends more distally than the second side 142. As such, the first side 140 of the tapered wedge 102(1) can be characterized as a leading side 140, and the second side 142 of the tapered wedge 102(1) can be characterized as a lagging side 142. In the case of the blunt-nosed wedge 102(2), the first and second sides 140 and 142 are about the same length, and neither can be considered distal or proximal relative to the other.

In the illustrated embodiment, the first and second sides 140 and 142 are substantially flat and parallel to each other (see FIG. 6), so that when stacked on top of each other to form the wedge stack 134, as shown in FIG. 5, the wedges 102 will be parallel to each other and the center of the wedge stack 134(1) will be directed along a straight line (that is, a linear stacking arrangement is formed), as illustrated in FIG. 8. In this manner, the height of the wedge stack 134 will be maximized with a minimum number of wedges 102. Alternatively, the second sides 142 are curved (see FIG. 7), so that when stacked on top of each other to form the wedge stack 134, the wedges 102 will be offset from each other in all directions, thereby forming a distributed stack 134(2), as illustrated in FIG. 9. In this case, the force applied to the surrounding bone structure will be more distributed, thereby minimizing the risk of fracturing previously healthy portions of the bone structure.

As shown in FIG. 3, the tapered wedge 102(1) includes a tapered side 144 located between the distal ends of the leading and lagging sides 140 and 142, thereby forming a point 146 between the leading side 140 and tapered side 144. As illustrated in FIG. 5, when a pair of tapered wedges 102(1) are placed back-to-back to form a wedge pair 132, the points 146 of the respective wedges 102(1) form a pointed nose 148 that facilitates insertion of the wedge pair 132 between another wedge pair 132, as will be described in further detail below. In the case of a wedge pair 132, two opposing wedge surfaces are provided for separating and driving the other wedge pair 132 apart, as illustrated in FIG. 5. In the preferred embodiment, the tapered side 144 can be substantially flat or slightly curved in the longitudinal direction to facilitate sliding between the tapered side 144 and the second side 142 of another wedge 102. Preferably, the tapered side 144 is substantially flat in the lateral direction (into the paper), so that it is capable of sliding along the flat first side 140 of another wedge 102 in a manner that maintains lateral alignment between the respective wedges 104. In this case, a linear stacking arrangement, such as the stack 134(1) illustrated in FIG. 8, can be formed. If a more distributed stacking arrangement, such as the stack 134(2) illustrated in FIG. 9, is desired, the tapered side 144 can be curved in the lateral direction. Whichever type of stacking arrangement is used, the significance is that the stack 132 grows in height as wedges 102 are added.

As shown in FIG. 4, the blunt-nosed wedge 102(2) includes a blunted side 150 located between the distal ends of the leading and lagging sides 140 and 142. The blunted side 150 minimizes trauma to the bone structure, e.g., the anterior wall of the vertebra 200 if the wedge 102(2) is being introduced through the posterior wall of the vertebra 200. As will be described in further detail below, a wedge pair 132 composed of two of the blunt-nosed wedges 102(2), will typically be the first wedge pair 132 introduced into the vertebra 200, and therefore would not be used to drive another wedge pair apart. As such, it is consequential that the blunt-nosed wedges 102(2) are not particularly configured for insertion between other wedges.

Each wedge 102 includes a driven side 152 located between the proximal ends of the first and second sides 140 and 142 for engaging the wedge driver 106. The driven side 152 is substantially flat and parallel to the first and second sides 140 and 142, so that the wedge driver 106 may fully engage the wedge 102. Each wedge 102 also includes a notch 154 located between the driven side 152 and the first side 140. When a pair of wedges 102 are placed back-to-back to form a wedge pair 132, the notches 154 of the respective wedges 102 form a single indentation 156 (shown in FIG. 5) that receives the nose 148 of another wedge pair 132, thereby facilitating separation of the wedge pair 132. The indentation 156 of the wedge pair 132 is also configured to receive the ridge 130 of the driver head 129. In this manner, the proper rotational orientation of the wedge pair 132 can be maintained with the wedge driver 106 as the wedge pair 132 is traveling through the cannula lumen 118. Alternatively, the cannula lumen 118 can be keyed, or otherwise have a non-circular shape that matches the profile of the wedge pair 132, in order to fix the rotational orientation of the wedge pair 132.

Referring to FIG. 10, another wedge 102(3) is described. The wedge 102(3) is similar to the tapered wedge 102(1), with the exception that it includes an optional notch 158 formed along the proximal portion of the first side 140. A bearing side 160 is formed at the distal portion of the notch 158. The second side 142 of the wedge 102(3) is also raised to form a bearing side 166 between the second side 142 and the tapered side 144. Thus, when two wedges 102(3) are slid together, the raised second side 142 of one of the wedges 102(3) will travel along the notch 158 of another wedge 102(3) until the bearing sides 160 and 162 contact each other. In this manner, distal movement of the wedges 102(3) will be limited, thereby minimizing damage that may otherwise be caused by a wedge 102 impinging on the distal portion of the bone structure.

The above described wedges 102 may be porous and/or fenestrated in order to improve the osteoconductivity or osteoinductivity of the substrate materials. Likewise, appropriately porous and fenestrated wedges may become carriers for phramaceuticals, antibiotics, orthobiologics (bone morpogenetic proteins (BMP)) and bone growth factors (e.g., TGF-$\beta$, IGF-I, IGF-II, AGF, etc) and any other therapeutic medium known in the art. Biomechanically, porosity and fenestrations will allow the bony defect and the wedge implants to be infiltrated and locked into position with any bone cement or other physiological medium. The wedges will interlock as a bone cement or other medium is injected and extrudes into the interstices of the porous surfaces or fenestrations.

Referring back to FIG. 2, the plunger assembly 108 includes a plunger head 164, which is configured to be slidably received into the cannula lumen 118, and a plunger shaft 166 on which the plunger head 164 is mounted. The plunger shaft 166 can be disposed within the cannula lumen 118, allowing for the user to longitudinally displace the plunger head 164 within the cannula lumen 118. The proximal end of the plunger shaft 166 may be coupled to any appropriate controller means to aid in proximal displacing the plunger head 164. Alternatively, the plunger head 164 may be manually displaced.

The plunger shaft 166 is preferably flexible, allowing it to conform to any curves in the cannula shaft 112 without breaking. It may be composed of the same materials as the cannula shaft 112. Alternatively, the plunger shaft 166 may be made from a cable or braided material composed of a suitable material, such as titanium. Ultimately, the type of material selected for the plunger shaft 166 will depend on the viscosity of the therapeutic media 110 to be implanted within the vertebra 200. For example, a highly viscous material, such as some bone cements, may require a plunger shaft 166 with a high tensile strength, such as braided titanium.

The treatment media 110 may include granular implants or particles, such as "calcium salts," including Amorphous Calcium Phosphate (ACP), Tricalcium Phosphate (TCP), and $CaSO_4$, $CaPO_4$, Hydroxylapatite (HA), Calcium Aluminate, etc. The treatment media 110 may also include bone cement, such as PMMA or the like, and other biomaterials, such as donor tissue. The implants or particles or granules within the treatment media 110 may have approximately the same size, or alternatively, may have a distribution of sizes.

Figure 11:
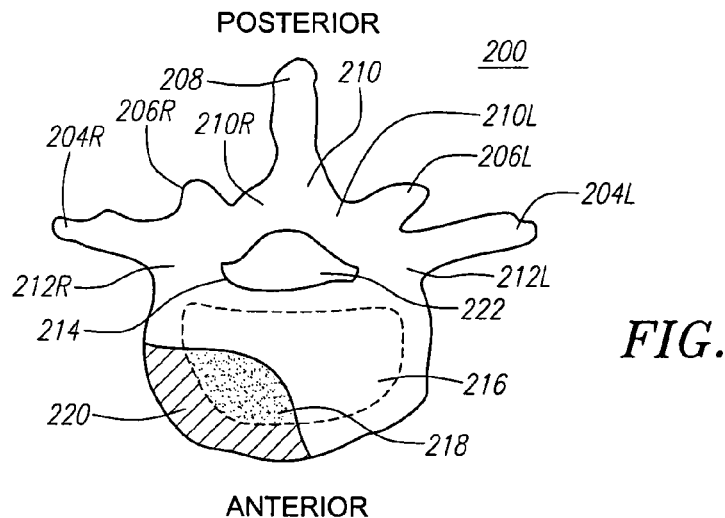
FIG. 11 is a partially cut-away top view of a lumbar vertebra.

Although, as noted above, use of the bone fracture treatment kit 100 is not limited to treatment of vertebral ailments, such procedures are discussed here for exemplary purposes. Before discussing such methods of operation, various portions of the vertebra are briefly discussed. Referring to FIG. 11, the posterior of the vertebra 200 includes right and left transverse processes 204R, 204L, right and left superior articular processes 206R, 206L, and a spinous process 208. The vertebra 200 further includes a centrally located lamina 210 with right and left lamina 210R, 210L, that lie in between the spinous process 208 and the superior articular processes 206R, 206L. Right and left pedicles 212R, 212L are positioned anterior to the right and left transverse processes 204R, 204L, respectively. A vertebral arch 214 extends between the pedicles 212 and through the lamina 210. The anterior of the vertebra 200 includes a vertebral body 216, which joins the vertebral arch 214 at the pedicles 212. The vertebral body 216 includes an interior volume of reticulated, cancellous bone 218 enclosed by a compact cortical bone 220 around the exterior. The vertebral arch 214 and vertebral body 216 make up the spinal canal, i.e., the vertebral foramen 222, which is the opening through which the spinal cord and epidural veins pass.

Referring now to FIGS. 12-18, a method of using the kit 100 to treat a compression fracture 202 within a vertebra 200 will now be described. First, the physician inserts the cannula 104 into the vertebral body 216 using any one of a variety of approaches. For example, as depicted in FIG. 12A, in a transpedicular approach, access to the cancellous bone 218 in the vertebral body 216 is gained through the pedicles 212. Alternatively, as depicted in FIG. 12B, a parapedicular approach may be used in which access is gained through the side of the vertebral body 216 beside the pedicles 212. This approach may be selected if the compression fracture 202 has resulted in the collapse of the vertebral body 216 below the plane of the pedicles 212. Still other physicians may opt for an intercostals approach through the ribs (not shown) or a more clinically challenging anterior approach (not shown) to the vertebral body 216.

Figure 13:
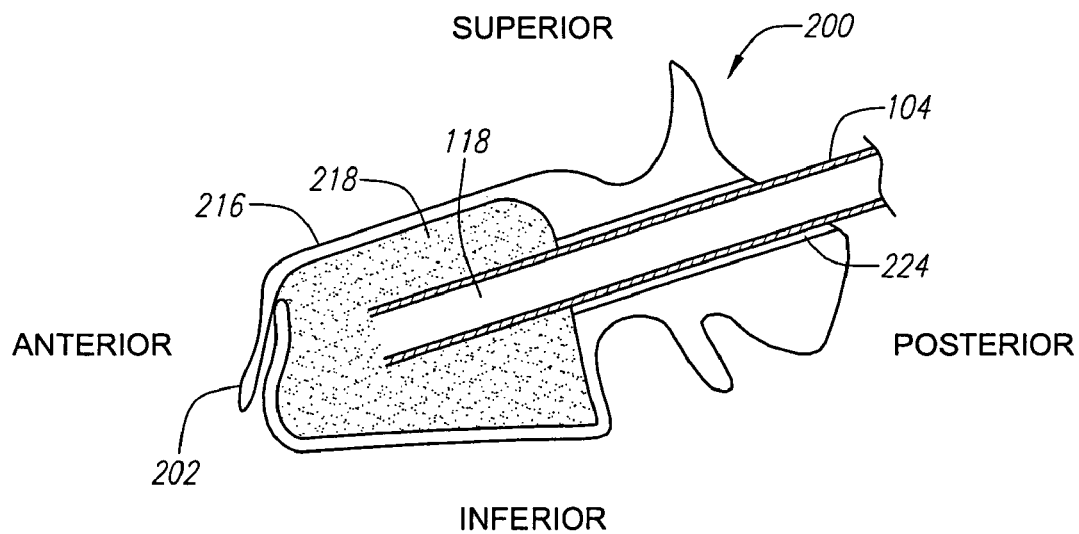
FIGS. 13-18 are lateral views of a method of using the treatment kit of FIG. 2 to treat a vertebra with a compression fracture.

In any event, access to the interior of the vertebral body 216 can be gained by using the cannula 104 to bore into the vertebra 200, thereby creating a channel or passage 224 that houses the cannula 104, as illustrated in FIG. 13. Torsional and/or axial motion may be applied to the cannula 104 to facilitate boring of the vertebra 200. The torsional and/or axial motion may be applied manually or mechanically (i.e., by a machine). An object, such as a hammer or a plunger, may also be used to tap against the proximal end 116 of the cannula 104 in order to facilitate boring into the vertebra 200. Alternatively, a stilette that can be introduced through the cannula lumen 118 can be used to create the passage 224, or a separate drill can be used to bore the passage 224 prior to placement of the cannula 104. Even more alternatively, the cannula 104 can be introduced into the interior of the vertebral body 216 through a naturally occurring bore or passage 224 in the vertebra 200 formed as a result of the compression fracture 202.

Figure 14:
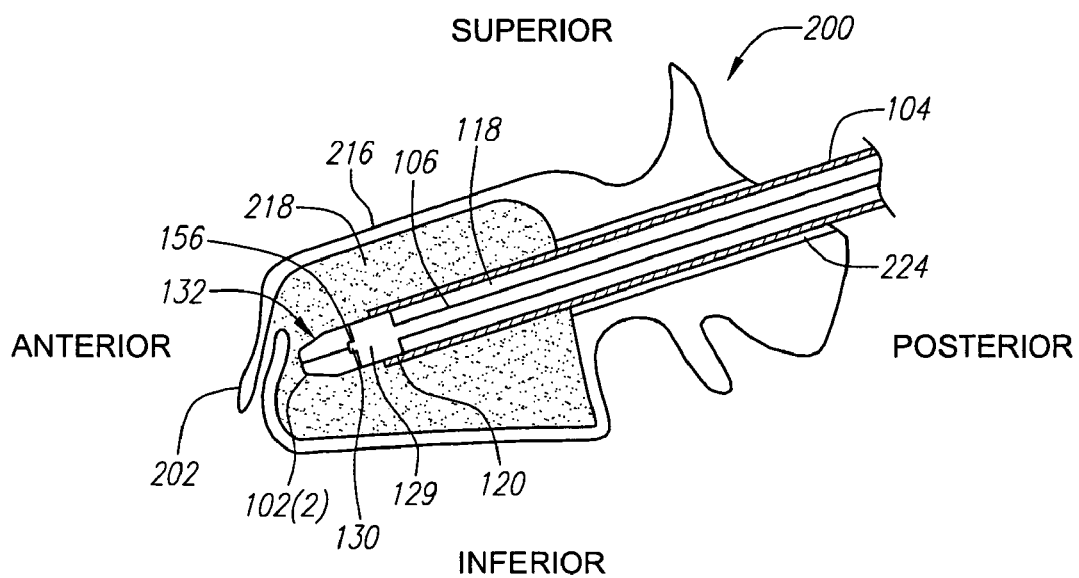

The distal end 114 of the cannula 104 is preferably placed at the anterior of the vertebral body 216 to provide maximum leverage in reducing the fracture 202. Once the cannula 104 has been properly placed, a wedge pair 132 formed by blunt-nosed wedges 102(2) is introduced into the cannula lumen 118, the wedge driver 106 is inserted into the cannula lumen 118 and engaged with the wedge pair 132 with the ridge 130 of the driver head 129 being received within the indentation 156 formed by the notches 154 of the wedges 102(2) (shown best in FIG. 5), and the driver 104 is then distally pushed through the cannula lumen 118 to convey the wedge pair 132 through the cannula lumen 118, and out the exit port 120 into the cancellous bone 218 of the vertebral body 216, as illustrated in FIG. 14.

Figure 15:
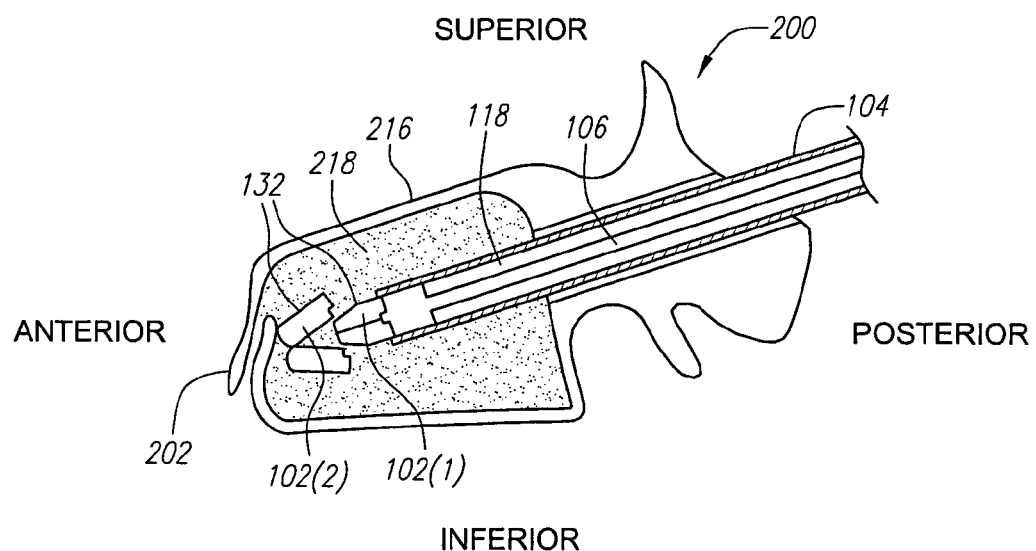
Figure 16:
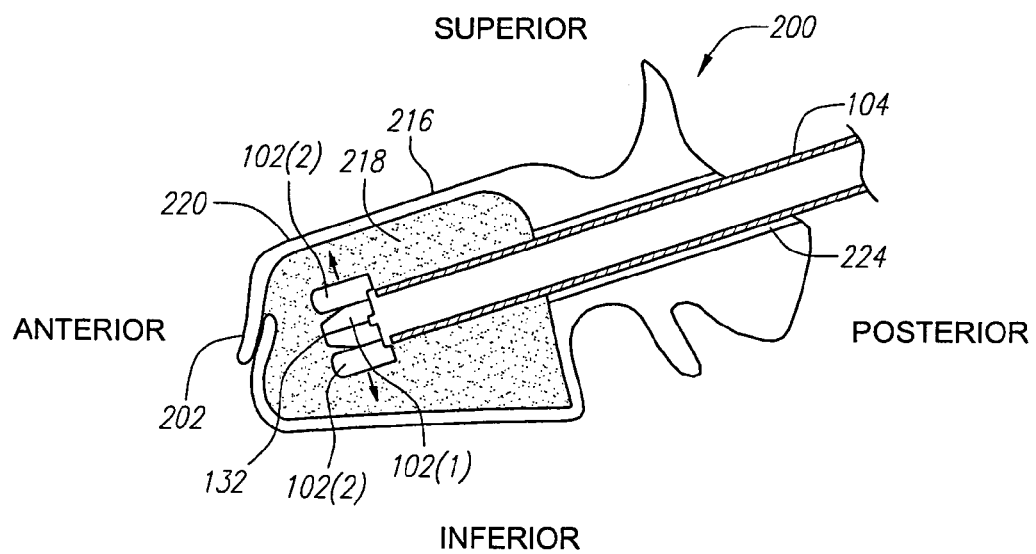

The wedge driver 106 is then removed from the cannula lumen 118, and the process is then repeated using another wedge pair 132 formed by tapered wedges 102(1). As illustrated in FIG. 15, upon exiting the cannula lumen 120, the nose 148 of the subsequent wedge pair 132 engages the indentation 156 of the preceding wedge pair 156 (shown best in FIG. 5), thereby causing the proximal end of the preceding wedge pair 132 to split apart. As illustrated in FIG. 16, the subsequent wedge pair 132 is slid between the preceding wedge pair 132. Specifically, the tapered sides 144 of the subsequent wedge pair 132 slidably engage the respective second sides 142 of the preceding wedge pair 132 (shown best in FIG. 5), thereby driving the preceding wedge pair 132 apart. As a result, separation of the preceding wedge pair 132 in opposite directions will in turn compress the cancellous bone 218 against the cortical bone 220, thereby displacing the superior and inferior sides of the vertebra 200 in opposite directions to reduce the compression fracture 202.

Preferably, during placement of the subsequent wedge pair 132, the proximal end of the wedge driver 106 is tapped slightly to drive the subsequent wedge pair 132 between the preceding wedge pair 132 so as to minimize anterior movement of the preceding wedge pair 132. Tapping may be manually accomplished, e.g., by using a hammer, or mechanically accomplished, e.g., by using a vibrator. If the optional wedges 102(3) illustrated in FIG. 10 are used, anterior movement of the subsequent wedge pair 132 will be limited by the preceding wedge pair 132. That is, the bearing surfaces of the optional notches 158 will engage each other to prevent anterior movement.

It should be noted that initial movement of the superior and inferior sides of the vertebra 200 will depend upon the nature and age of the compression fracture 202. For example, if the compression fracture 202 is relatively new, it will take a relatively small amount of force to displace the superior and inferior sides of the vertebra 200 in opposite direction. In this case, the compression fracture 202 may immediately begin to reduce in response to the separate of the preceding wedge pair 132. If on the other hand the compression fracture 202 is relatively old, and thus partially fused, it will take a relatively large amount of force to displace the superior and inferior sides of the vertebra 200 in opposite directions. In this case, the compression fracture 202 may only begin to reduce in response to movement of the preceding wedge pair directly against the cortical bone 220, e.g., after several wedge pairs 132 have been introduced into the vertebral body 216.

Figure 17:
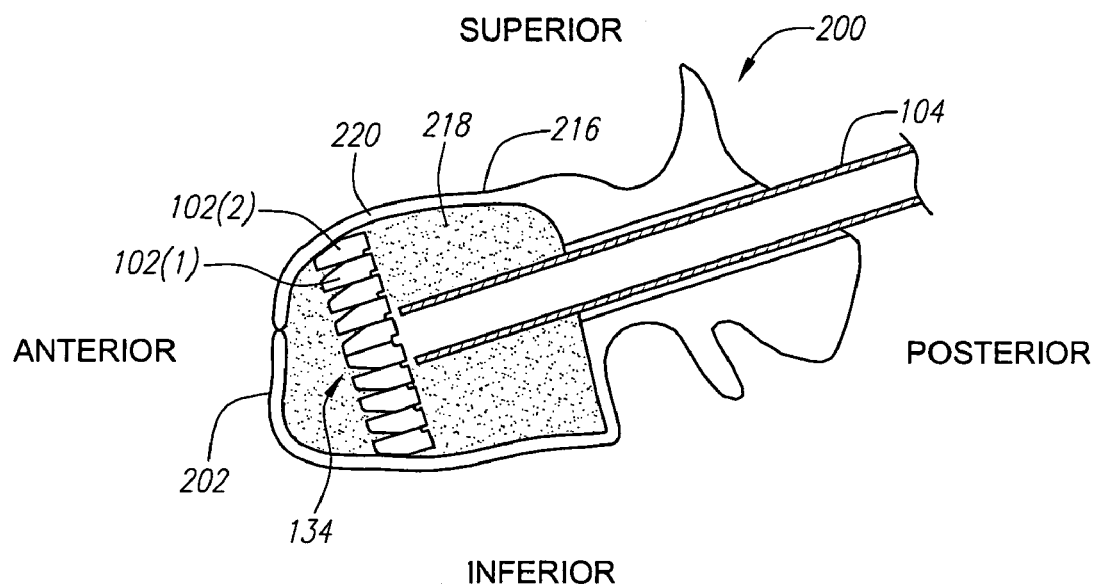

As illustrated in FIG. 17, this process is repeated to construct a wedge stack 134, such as those illustrated in FIGS. 8 and 9, thereby completely reducing the compression fracture 202. If the compression fracture 202 has not been completely reduced, or alternatively if further support within the vertebral body 216 is need, additional wedge stacks can be created by repeating the foregoing steps with additional wedges. Additional passages 224 may need to be bored through the vertebra 200 in order access other regions of the vertebral body 216. It should be noted that although the wedge pairs 132 have been described as being iteratively introduced into the vertebra 200 in the above process (i.e., each wedge pair 132 is introduced into the cannula 106 and placed within the vertebra 200 before the next wedge pair 132 is introduced into the cannula 106), several wedge pairs 132 can be introduced into the cannula 106 followed by the introduction of the wedge driver 106. In this case, the entire wedge stack 134, or at least a large portion of it, can be constructed by distally displacing the wedge driver 106 through the cannula lumen 118 without reloading the cannula 104. In this manner, the time required to reduce the compression fracture 202 may be minimized.

Figure 18:
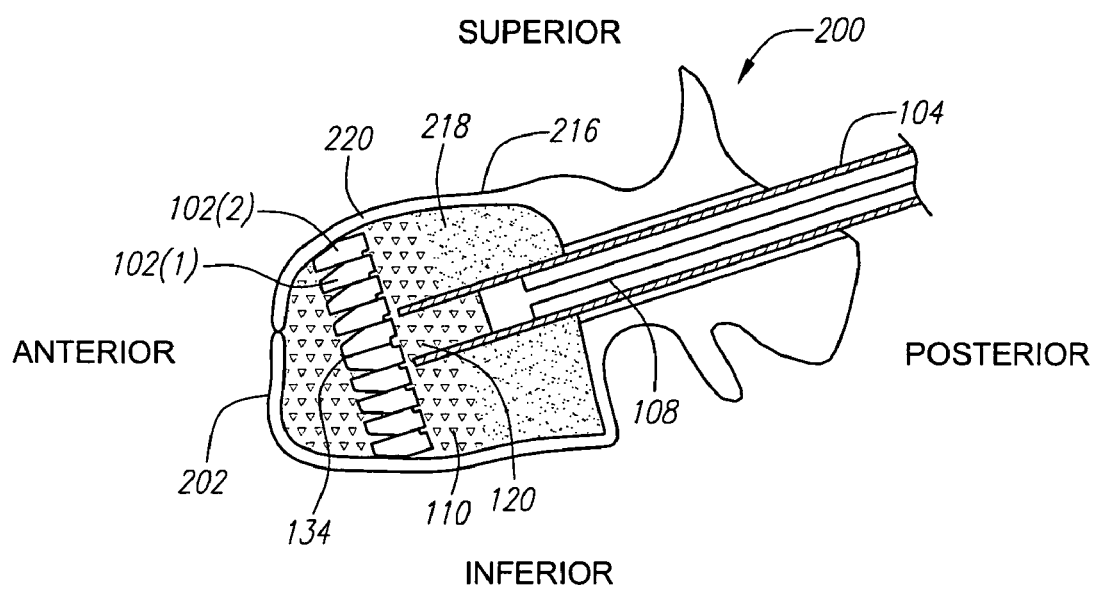

After reduction of the compression fracture 202 has been completed, the therapeutic media 110, and then the plunger assembly 108, is introduced into the cannula lumen 118. The plunger assembly 108 is then distally displaced within the cannula lumen 118, thereby forcing the therapeutic media 110 through the cannula lumen 118, out the exit port 120, and into the interior of the vertebral body 216, as illustrated in FIG. 18. The therapeutic media 110 flows between the wedges 102 and into any surface porosity or fenestration, and hardens, thereby providing increased structural integrity for the vertebra 200.

Figure 19:
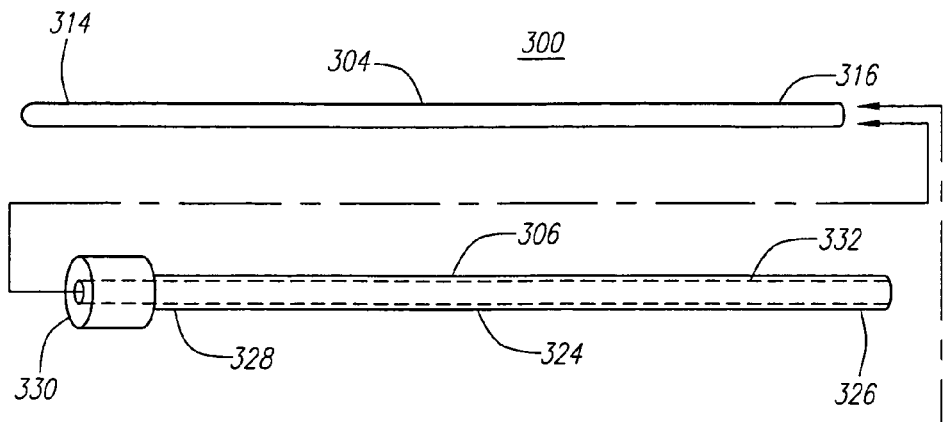
FIG. 19 is a plan view of a bone fracture treatment kit constructed in accordance with another preferred embodiment of the present inventions.

Referring to FIG. 19, a bone fracture treatment kit 300 constructed in accordance with another preferred embodiment of the present inventions is illustrated. Like the previously described kit 100, the kit 300 can be used for treating a bone compression fracture, and specifically, a compression fracture 202 within a vertebra 200 (shown in FIGS. 23-28). In performing this function, the kit 300 generally comprises a plurality of fracture reducing wedges 302 (only one shown in FIG. 19), a delivery member, and specifically a guide member 304, over which the wedges 302 can be guided, and a wedge driver 306 for pushing the wedges 302 over the guide member 304 into the vertebra 200 in order to reduce the compression fracture 202. In order to stabilize and set the vertebra 200, the kit 300 may optionally include a cannula, plunger assembly, and therapeutic medium similar to the previously described cannula 104, plunger assembly 108, and therapeutic medium 110, with the exception that the cross-sectional size of the cannula can be made smaller, since it need not accommodate the wedges 302.

Figure 20:
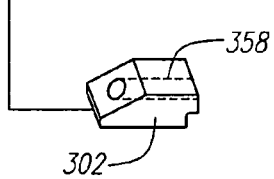
FIG. 20 is a tapered wedge that can be used in the treatment kit of FIG. 19.
Figure 20:
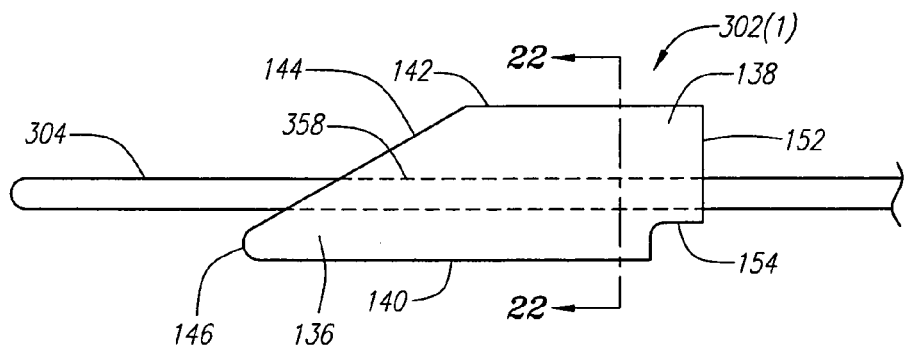
Figure 21:
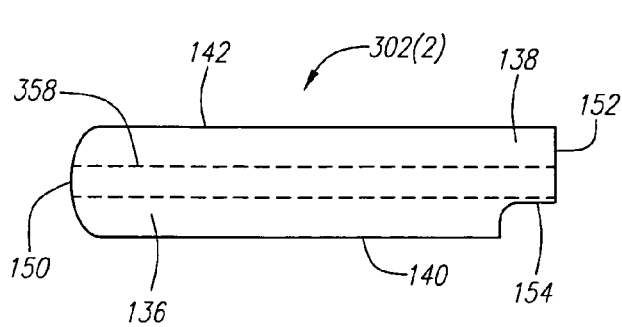
FIG. 21 is a blunt-nosed wedge that can be used in the treatment kit of FIG. 19.

The wedges 302 are similar in geometry and structure to the previously described wedges 102, and to the extent that the elements of the wedges 302 are identical to those of the wedges 102, identical reference numbers have been used. As illustrated in FIGS. 20 and 21, each wedge 302 can take the form of a tapered wedge 302(1) or a blunt-nosed wedge 302(2). The wedges 302 substantially differ from the wedges 102 in that each wedge 302 comprises a longitudinal bore 358 (shown in phantom) extending through the body of the wedge 102 between the driven side 152 and tapered edge 144 (in the case of a tapered wedge 302(1)), or between the driven side 152 and the blunted side 150 (in the case of a blunt-nosed wedge 302(2)). The bore 358 is sized to receive the guide member 304, so that the respective wedge 302 can be guided over the guide member 304. Preferably, the bore 358 is centered about the neutral axis 360 of each wedge 302. In this manner, the structural integrity of the wedge 302 is not compromised, since the neutral axis 360 is not the source of strength for the wedge 302.

Returning to FIG. 19, the guide member 304 is preferably stiff (e.g., it can be composed of a stiff material, or reinforced with a coating or a coil to control the amount of flexing) to facilitate accurate guidance of the wedges 302 within the vertebra 200. The materials used in constructing the guide member 304 may comprise any of the variety of biocompatible materials, e.g., those previously discussed with respect to the cannula 104. In the illustrated embodiment, the distal tip of the guide member 304 is blunt to minimize any trauma caused within the vertebra 200.

Figure 22:
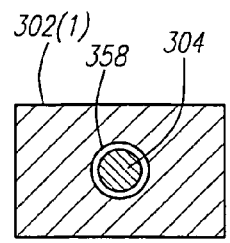
FIG. 22 is a cross-sectional view of the tapered wedge of FIG. 20, along with a guide member, taken along the lines 22-22.
Figure 23:
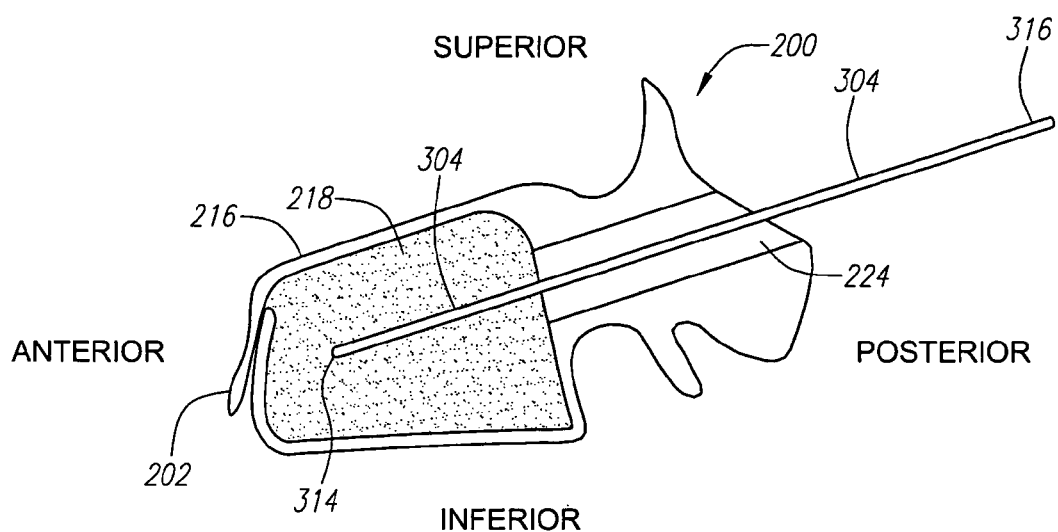
FIGS. 23-28 are lateral views of a method of using the treatment kit of FIG. 19 to treat a vertebra with a compression fracture.

As illustrated in FIG. 22, the guide member 304 and the bore 358 of the wedge 302 preferably have non-circular cross-sections (and in this case, oval cross-sections) that are geometrically similar to each other. In this manner, rotational alignment of the wedge 302 can be achieved, i.e., the wedge 302 will be rotationally fixed relative to the guide member 304. Preferably, the cross-sectional size of the guide member 304 is selected such that the guide member 304 is laterally stiff enough to provide accurate guidance of the wedges 302 into the vertebra 200.

It can be appreciated that the use of a guide member over which each wedge 302 is introduced, as opposed to a cannula through which each wedge 302 may be introduced, reduces the effective size of the access passage drilled through the cortical bone 220 of the vertebra 200. That is, the cross-sectional size of the access passage can be reduced by a dimension equal to twice the thickness of a cannula wall. Basically, the size of the access passage need only be large enough to pass a single wedge 302. As a result, the trauma caused to the vertebra 200 is reduced. Alternatively, the use of a guide member allows the size of the wedges 302 to be advantageously increased without increasing the size of the access passage that would otherwise be used to introduce a standard cannula.

Returning to FIG. 19, the wedge driver 306 comprises a driver shaft 324 having a proximal end 326 and distal end 328, and a driver head 330 formed at the distal end 328 of the shaft 324. The wedge driver 306 also comprises a longitudinal bore 332 (shown in phantom) extending through the entire length of the driver shaft 324. The bore 332 is sized to receive the guide member 304, so that the wedge driver 306 can slidingly engage the guide member 304. The wedge driver 306 may be composed of any suitable rigid material, e.g., those previously described with respect to the wedge driver 106.

Figure 12A:
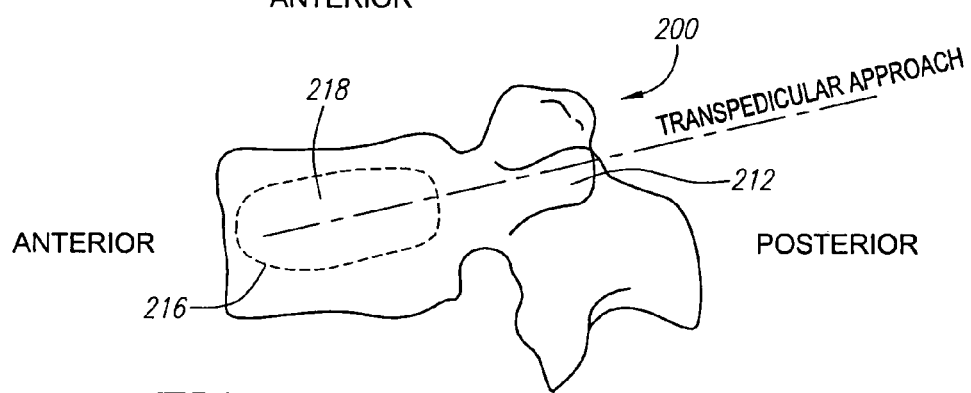
FIG. 12A is a lateral view of posterior transpedicular access route to the anterior vertebral body shown in FIG. 11.
Figure 12B:
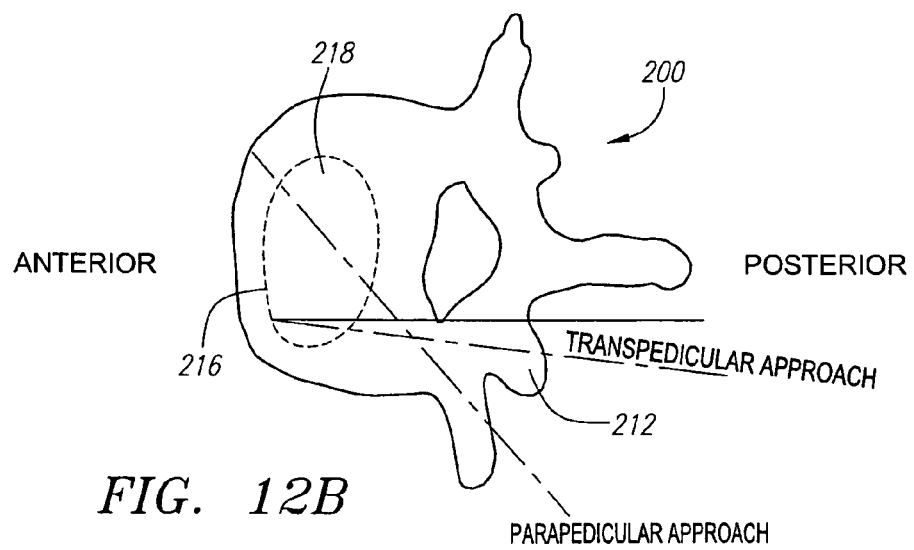
FIG. 12B is a top view of posterior transpedicular and parapedicular access routes to the anterior vertebral body shown in FIG. 11.

Referring now to FIGS. 23-28, a method of using the kit 300 to treat a compression fracture 202 within a vertebra 200 will now be described. First, the physician inserts the guide member 304 into the vertebral body 216 via a passage 224 (FIG. 24) using any one of a variety of approaches, e.g., a transpedicular approach (FIG. 12A) or parapedicular approach (FIG. 12B). The passage 224 can be formed using any one of the previously described techniques. The distal end 314 of the guide member 304 is preferably placed at the anterior of the vertebral body 216 to provide maximum leverage in reducing the fracture 202.

Figure 24:
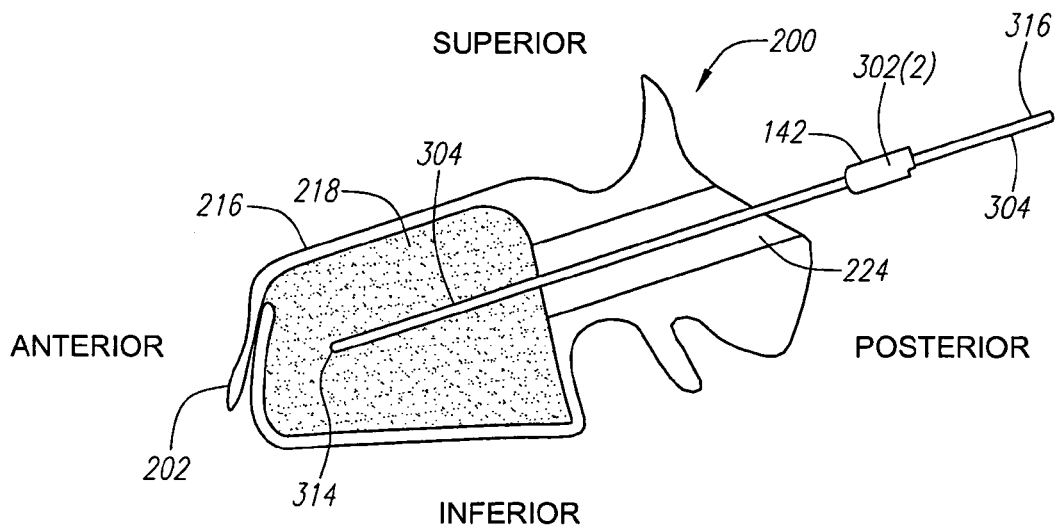

Once the guide member 304 has been properly placed, a blunt-nosed wedge 302(2) is introduced over the guide member 304 by threading the proximal end 314 of the guide member 304 through the longitudinal bore 358 of the respective wedge 302(2) (FIG. 24). Preferably, the wedge 302(2) is rotationally aligned with respect to the guide member 304, such that the second side 142 of the wedge 302(2), when introduced into the vertebral body 216, faces towards one of the superior or inferior sides of the vertebra 200. The non-circular cross-sections of the respective guide member 304 and bore 358 will maintain rotational alignment of the wedge 302(2). Thus, the wedge 302(2) will be properly oriented within the vertebra 200 as long as the guide member 304 is not rotated.

Figure 25:
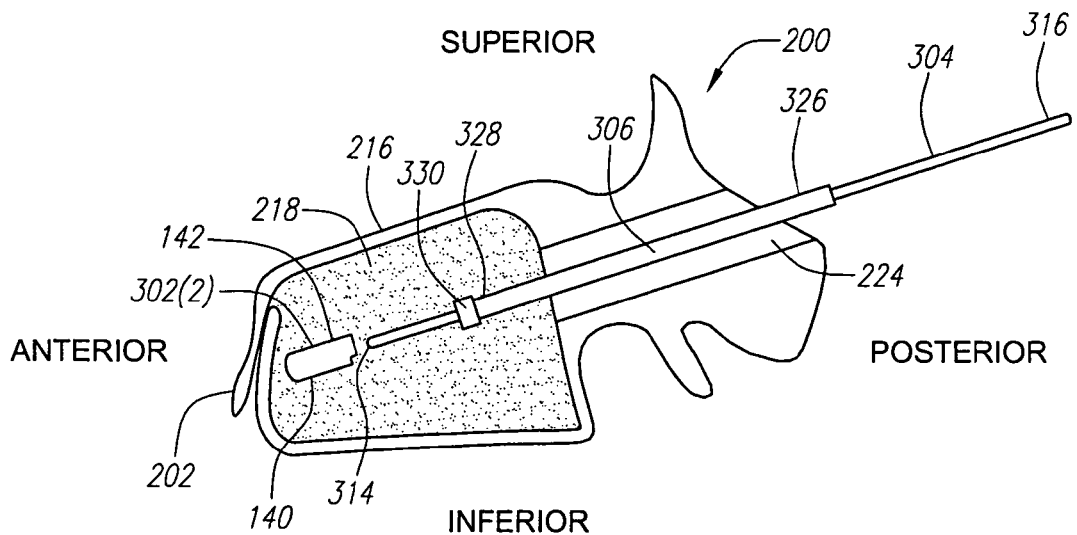

Next, the wedge driver 306 is introduced over the guide member 304 by threading the proximal end of the guide member 304 through the longitudinal bore of the respective driver 306. The driver 306 is then distally pushed over the guide member 304 to engage the driver head 330 with the driven side 152 of the wedge 302(2), thereby displacing the wedge 302(2) from the distal end 314 of the guide member 304 and into the cancellous bone 218 of the vertebral body 216 (FIG. 25). As illustrated, the second side 142 of the wedge 302(2) is facing the superior side of the vertebral body 216.

Figure 26:
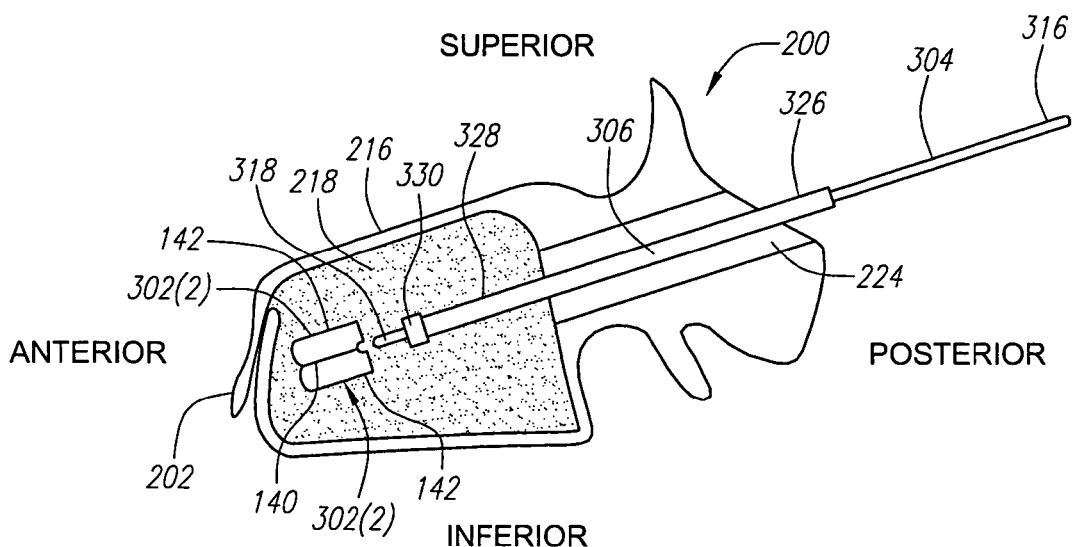

Next, another blunt-nosed wedge 302(2) is introduced over the guide member 304 and into the cancellous bone 218 adjacent the first side 140 of the first wedge 302(2) to form a wedge pair with an upper wedge 302(2) and lower wedge 302(2) (FIG. 26). This is accomplished in the same manner as the upper wedge 302(2) was introduced, with the exception that the second side 142 of the lower wedge 302(2) faces the inferior side of the vertebral body 216.

Figure 27:
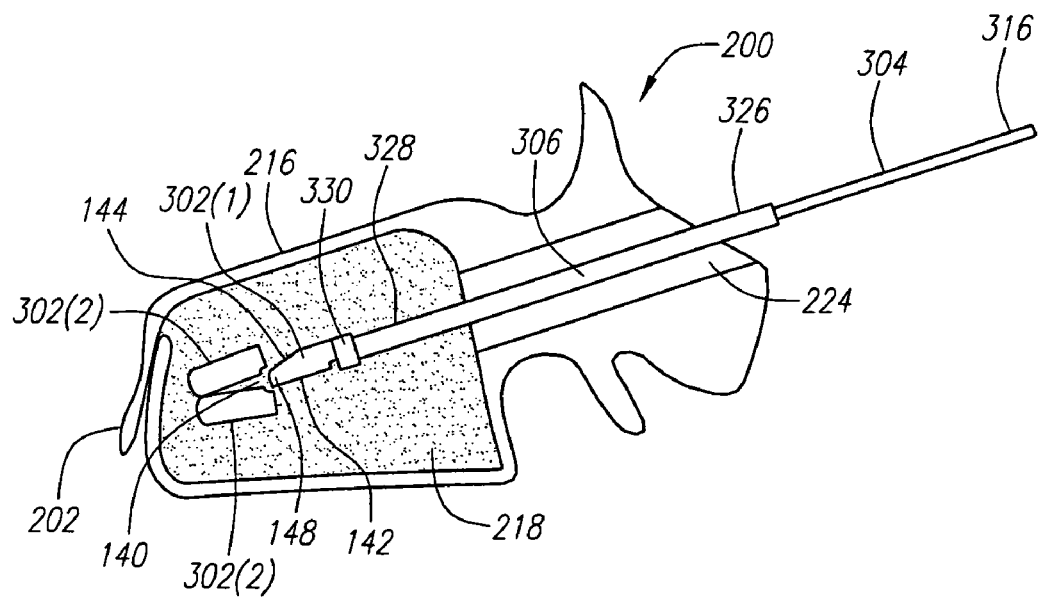

Next, a tapered wedge 302(1) is introduced over the guide member 304 and into the cancellous bone 218, so that the nose 148 of the wedge 302(1) engages an indentation formed between the wedge pair, thereby causing the upper and lower wedges 302(2) to split apart (FIG. 27). Specifically, the tapered wedge 302(1) is introduced into the cancellous bone 218, such that the second side 142 faces either of the superior or inferior sides of the vertebral body 206—in this case, the superior side. As the tapered wedge 302(1) is introduced, the tapered side 144 of the wedge 302(1) slidably engages the first side 140 of upper wedge 302(2) to displace the upper and lower wedges 302(2) in opposite direction, which in turn compresses the cancellous bone 218 against the cortical bone 220. As a result, the superior and inferior sides of the vertebra 200 are displaced in opposite directions to reduce the compression fracture 202. Preferably, during placement of the subsequent wedge 302(1), the proximal end 326 of the wedge driver 106 is tapped slightly to drive the subsequent wedge 302(1) between the upper and lower wedges 302(2) so as to minimize anterior movement of the upper and lower wedges 302(2).

Figure 28:
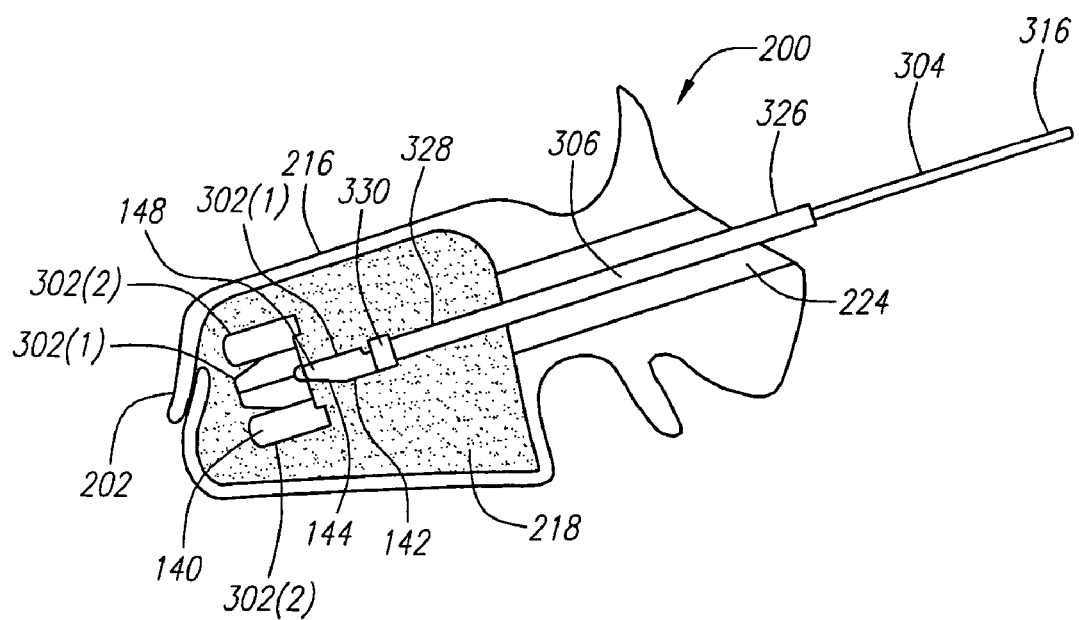

Next, another tapered wedge 302(1) is introduced over the guide member 304 and into the cancellous bone 218, so that the nose 148 of the wedge 302(1) engages an indentation formed between the preceding tapered wedge 302(1) and the lower blunt-nosed wedge 302(2), thereby causing the upper and lower wedges 302(2) to further split apart (FIG. 28). Specifically, the tapered wedge 302(1) is introduced into the cancellous bone 218, such that the second side 142 faces the inferior side of the vertebra 200. As the tapered wedge 302(1) is introduced, the tapered side 144 slidably engages the first side 140 of lower wedge 302(2), thereby displacing the upper and lower wedges 302(2) further apart to further reduce the compression fracture 202.

This process is repeated with subsequent tapered wedges 302(1) to construct a wedge stack, thereby completely reducing the compression fracture 202 in the same manner as previously described with respect to FIG. 17. After reduction of the compression fracture 202 has been completed, therapeutic media can be optionally introduced through a cannula and into the interior of the vertebral body 216 in the same manner previously described with respect to FIG. 18, thereby providing increased structural integrity for the vertebra 200. Notably, the cannula can be made smaller than the previously described cannula 106, since it will not be used to introduce wedges 302 into the vertebral body 216.

It should be noted that although the wedges 302(1) have been described as being iteratively introduced into the vertebra 200 in the above process (i.e., each wedge 302 is introduced over the guide member 304 and placed within the vertebra 200 before the next wedge 302 is introduced over the guide member 304, a series of wedges 302 can be introduced over the guide member 304 followed by the introduction over the wedge driver 306. In this case, the series of wedges 302 are threaded onto the guide member 304, such that the second sides 142 of the wedges 302, when introduced into the vertebral body 216, alternately face the superior and inferior sides of the vertebra 200.

Figure 29:
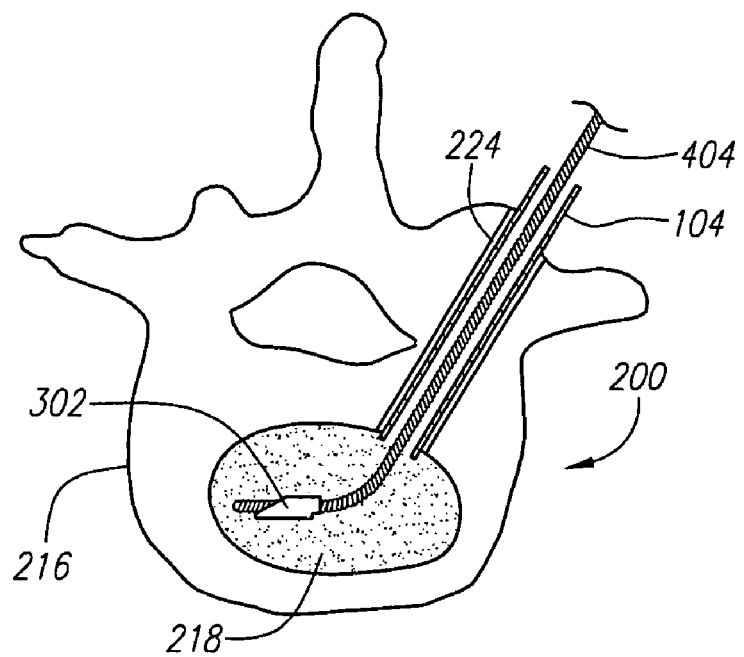
FIG. 29 is a partially cut-away top view of a lumbar vertebra, particularly showing the use of an alternative embodiment of a guide member to introduce a wedge within the vertebra.
Figure 30:
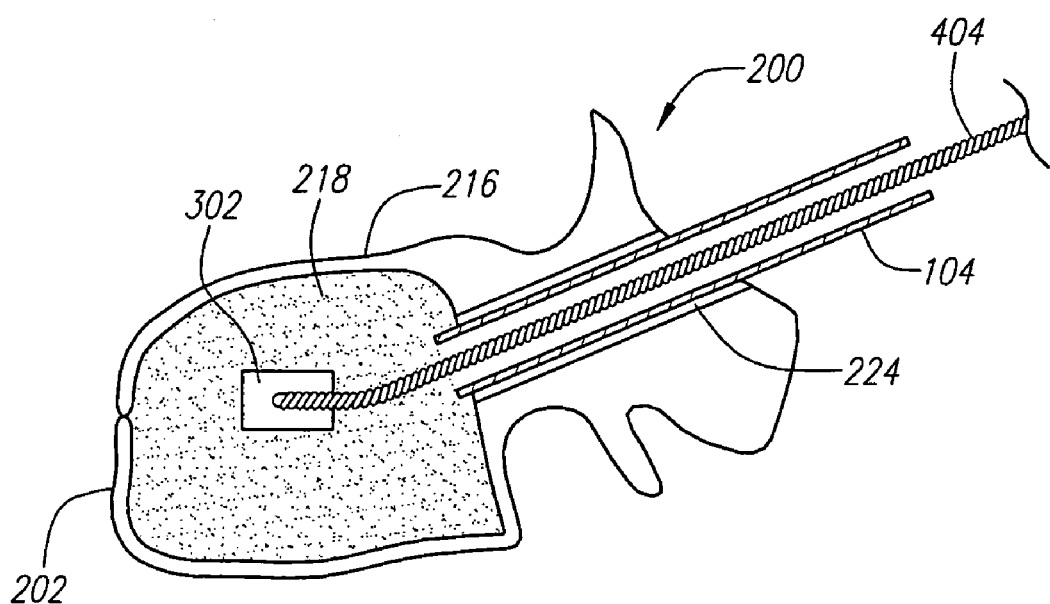
FIG. 30 is a lateral view of the lumbar vertebra, particularly showing the use of the guide member of FIG. 29.

Referring now to FIGS. 29 and 30, an alternative embodiment of a guide member 404 that can be used to introduce a series of wedges 302 into the vertebral body 216 is described. Rather than being composed of a rigid material like the previously described guide member 304, the guide member 404 is composed of a laterally flexible material, such as a wound stainless steel coil. The guide member 404 preferably has enough axial strength, such that it can be introduced through cancellous bone 218. Because the guide member 404 is laterally flexible, the wedges 302 can be located in regions of the vertebral body 216 that are not directly in line with the passage 224 through which the guide member 404 is introduced into the vertebral body 216. In this manner, the wedges 302 can be stacked in almost any region within the vertebral body 216 without boring another passage 224 through the vertebra 200.

In creating a wedge stack, the wedges 302 will be introduced over the guide member 404 in the same manner described above with respect to the guide member 304. The only difference is that the wedges 302 can be guided over the flexible guide member 304 in a curvilinear fashion, i.e., around curves. A lateral flexible wedge driver (not shown) can be used to push the wedges 304 along the guide member 304. As illustrated in the figures, a cannula 104 is preferably used to introduced the wedges 304 through the passage 224, so that the wedges 304 are not hindered by the sides of the passage 224 as they are being introduced over the guide member 404.

Figure 31:
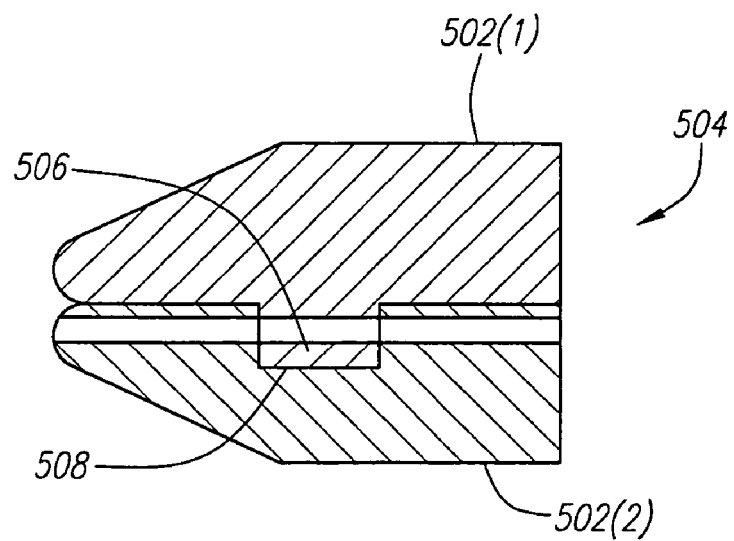
FIG. 31 is a side view of an alternative embodiment of a wedge pair that can be introduced over a guide member.
Figure 32:
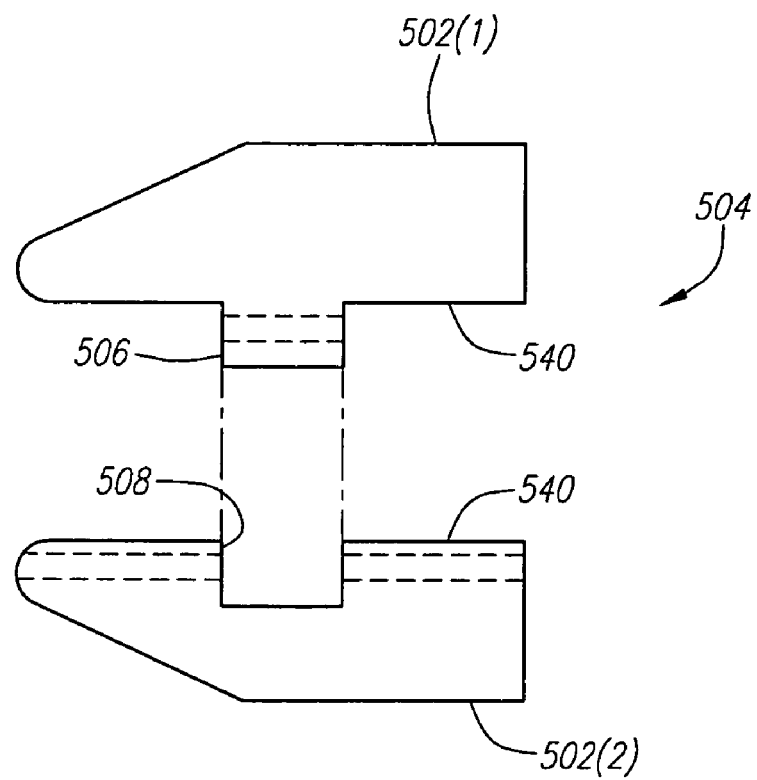
FIG. 32 is an exploded view of the wedge pair of FIG. 31.

Referring now to FIGS. 31 and 32, an alternative embodiment of a wedge 502, which can be used with the previously described rigid or flexible guide members, is described. Whereas the previous wedges 302 could only be introduced over a guide member in a serial arrangement, the wedges 502 can be introduced over a guide member as wedge pairs 504. To this end, the wedges 502 are designed, such that they fit together in a manner that axially aligns the longitudinal bores of the wedges 302. Specifically, two types of wedges 502 are provided: a male wedge 502(1) and a female wedge 502(2).

The male wedge 502(1) comprises a protuberance 506, and the female wedge 502(2) comprises a matching recess 508 that can receive the protuberance 506 when the respective leading sides 540 of the male and female wedges 502 are mated with each other. A longitudinal bore 354 extends through the protuberance 506 of the male wedge 502(1), and a similar longitudinal bore 356 extends through the entire length (including the recess 508) of the female wedge 502(2). Thus, when the male and female wedges 502 are mated together to form a wedge pair 504, the longitudinal bore 354 through the protuberance 506 axially lines up with the longitudinal bore 356 through the recess 508 to form a single longitudinal bore.

Thus, a mated wedge pair 504 can be introduced over a guide member by threading the guide member through this single longitudinal bore. The wedge pair 504 will be fastened together as long as the guide member is disposed within the longitudinal bore. When the wedge pair 504 is displaced from the distal end of the guide member, however, the mated wedge pair 504 is free to separate in opposite directions when force is applied between the wedge pair 504, e.g., using the nose of a subsequent wedge pair.

Although the use of longitudinal bores has been described in the context of introducing wedges over a guide member, the use of longitudinal bores within any device that is introduced into a bone structure may provide an advantageous benefit in reducing compression fractures by minimizing the effective size of the access passage through which the biocompatible device will be introduced, or alternatively maximizing the size of the biocompatible device without increasing the effective size of the access passage.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of treating a bone structure having opposing sides and a compression fracture therebetween, the method comprising introducing pairs of wedges into the bone structure in a direction lateral to the compression fracture, the wedges in each pair engaging each other in a side-by-side arrangement, wherein a subsequently introduced wedge pair is placed between an immediate previously introduced wedge pair, such that previously introduced pairs of wedges are displaced in opposite directions towards the respective opposing sides of the bone structure.

2. The method of claim 1, wherein the opposing sides of the bone structure are displaced in opposite directions as each subsequently introduced wedge pair is placed between an intermediate previously introduced wedge pair.

3. The method of claim 2, wherein the wedge pairs are introduced into the bone structure until the compression fracture has been completely reduced.

4. The method of claim 1, further comprising inserting a cannula into the bone structure, and introducing the wedge pairs through the cannula into the bone structure.

5. The method of claim 4, wherein the wedge pairs are introduced through the cannula by pushing the wedge pairs with a wedge driver.

6. The method of claim 1, wherein the bone structure is a vertebra.

7. The method of claim 1, wherein each wedge is composed of a biocompatible material.

8. The method of claim 7, wherein each wedge is composed of polymethylmethacrylate.

9. The method of claim 1, further comprising introducing treatment media into the bone structure after introduction of the wedge pairs.

10. The method of claim 1, wherein the wedges in the each pair mate with each other in the side-by-side arrangement.

11. The method of claim 10, wherein one of the wedges in the each pair has a protuberance and another of the wedges in the each pair has a recess sized to receive the protuberance.

12. A method of treating a bone structure having opposing sides and a compression fracture therebetween, the method comprising:
   introducing a guide member into the bone structure;
   threading the guide member through a longitudinal bore of each of a plurality of wedges;
   introducing wedges over the guide member in a direction lateral to the compression fracture, wherein a subsequently introduced wedge is placed in contact with a previously introduced wedge, such that previously introduced wedges are displaced in a direction towards one or both of the opposing sides of the bone structure wherein the wedges are introduced over the guide member by pushing the wedges with a wedge driver; and threading the guide member through a longitudinal bore of the wedge driver.

13. The method of claim 12, wherein the opposing sides of the bone structure are displaced in opposite directions as each subsequently introduced wedge is displaced.

14. The method of claim 12, wherein the wedges are introduced into the bone structure until the compression fracture has been completely reduced.

15. The method of claim 12, wherein the bone structure is a vertebra.

16. The method of claim 12, wherein each wedge is composed of a biocompatible material.

17. The method of claim 12, further comprising introducing treatment media into the bone structure after introduction of the wedges.

18. The method of claim 12, wherein the guide member is laterally rigid.

19. The method of claim 12, wherein the guide member is laterally flexible, and guide member is bent within the bone structure.

20. The method of claim 12, wherein the wedges are introduced over the guide member as wedge pairs.

21. The method of claim 20, wherein the wedges in each pair mate with each other in the side-by-side arrangement.

22. The method of claim 21, wherein one of the wedges in the each pair has a protuberance and another of the wedges in the each pair has a recess sized to receive the protuberance.

23. The method of claim 22, wherein the longitudinal bore of the one wedge extends through the protuberance, and the longitudinal bore of the other wedge extends through the recess, such that the longitudinal bores of the one wedge and the other wedge axially line up with each other when the wedges of the each pair are mated with each other.

24. A method of treating a bone structure having opposing sides and a compression fracture therebetween, the method comprising introducing wedges one pair at a time into the bone structure in a direction lateral to the compression fracture, wherein a subsequently introduced wedge pair is placed between an immediate previously introduced wedge pair, such that previously introduced pairs of wedges are displaced in opposite directions towards the respective opposing sides of the bone structure.

25. The method of claim 24, wherein the wedges in each pair engages each other in a side-by-side arrangement.

26. The method of claim 24, wherein the opposing sides of the bone structure are displaced in opposite directions as each subsequently introduced wedge pair is placed between an intermediate previously introduced wedge pair.

27. The method of claim 26, wherein the wedge pairs are introduced into the bone structure until the compression fracture has been completely reduced.

28. The method of claim 24, further comprising inserting a cannula or guide member into the bone structure, and introducing the wedge pairs through the cannula or over the guide member into the bone structure.

29. The method of claim 28, wherein the wedge pairs are introduced through the cannula or over the guide member by pushing the wedge pairs with a wedge driver.

30. The method of claim 24, wherein the bone structure is a vertebra.

31. The method of claim 24, wherein each wedge is composed of a biocompatible material.

32. The method of claim 31, wherein each wedge is composed of polymethylmethacrylate.

33. The method of claim 24, further comprising introducing treatment media into the bone structure after introduction of the wedge pairs.

34. The method of claim 24, wherein the wedges in the each pair mate with each other in the side-by-side arrangement.

35. The method of claim 24, wherein one of the wedges in the each pair has a protuberance and another of the wedges in the each pair has a recess sized to receive the protuberance.

* * * * *